US010610247B2

(12) United States Patent
Hopper et al.

(10) Patent No.: US 10,610,247 B2
(45) Date of Patent: Apr. 7, 2020

(54) SPRING-BIASED NASAL MOLDING DEVICE

(71) Applicants: Richard A. Hopper, Seattle, WA (US);
Thomas S. Johnston, Jr., Jacksonville, FL (US)

(72) Inventors: Richard A. Hopper, Seattle, WA (US);
Thomas S. Johnston, Jr., Jacksonville, FL (US)

(73) Assignee: SEATTLE CHILDREN'S HOSPITAL, Seattle, WA (US)

( * ) Notice: Subject to any disclaimer, the term of this patent is extended or adjusted under 35 U.S.C. 154(b) by 572 days.

(21) Appl. No.: 15/330,920

(22) Filed: Nov. 15, 2016

(65) Prior Publication Data

US 2017/0172593 A1 Jun. 22, 2017

Related U.S. Application Data

(63) Continuation-in-part of application No. 14/225,934, filed on Mar. 26, 2014, now Pat. No. 9,486,353.

(51) Int. Cl.
*A61B 17/24* (2006.01)
*A61F 5/08* (2006.01)

(52) U.S. Cl.
CPC ............. *A61B 17/24* (2013.01); *A61F 5/08* (2013.01)

(58) Field of Classification Search
CPC .......... A61B 17/24; A61B 90/02; A61C 9/00; A45F 2200/0516; A45F 5/02; A61F 5/08; A61F 5/566; A61F 5/56; A61F 2/0059; A61F 13/126; A61F 2013/00476; A61F 5/05891; D06F 55/00; F16B 2/22; G08B 3/1058; G08B 3/105; A61M 15/08; A61M 15/085; A61M 29/00; A61M 2210/0618; A61M 2025/0006; A61M 2025/0034; A61M 2025/0035; A61M 2025/0059; A61M 2025/0063; A61M 25/0014; A61M 25/0013; A61M 25/002; A61M 25/0021; A61M 25/0023; A61M 25/0026; A61M 25/0029; A61M 25/003; A61M 25/0041; A61M 25/0068; A61M 25/0293; Y10S 602/902; Y10S 623/902; A62B 23/06
See application file for complete search history.

(56) References Cited

U.S. PATENT DOCUMENTS

| 1,069,459 | A | 8/1913 | Myles |
| 5,361,459 | A | 11/1994 | Hyvonen et al. |
| 6,397,439 | B1 | 6/2002 | Langford |
| 8,323,308 | B2 | 12/2012 | Hopper |
| 8,523,896 | B2 | 9/2013 | Hopper |
| 2006/0260613 | A1* | 11/2006 | Pinter ..................... A61F 5/08 128/206.11 |
| 2007/0090251 | A1* | 4/2007 | Padden ..................... B60R 7/10 248/303 |

(Continued)

*Primary Examiner* — Wade Miles
*Assistant Examiner* — Mikail A Mannan
(74) *Attorney, Agent, or Firm* — Thomas C. Saitta

(57) ABSTRACT

A spring-biased nasal molding device for presurgical molding of cleft lip deformities, the device having a pair of intra-nasal shaping members for insertion into the nostrils and having an extra-nasal shaping member to be positioned external to the nostrils connected to each intra-nasal shaping member, wherein the intra-nasal and extra-nasal shaping members are brought together by the spring member to mold the nasal anatomy into the desired shape.

20 Claims, 3 Drawing Sheets

(56) References Cited

U.S. PATENT DOCUMENTS

| | | | |
|---|---|---|---|
| 2009/0099657 A1* | 4/2009 | Hopper | A61B 90/02 623/10 |
| 2011/0118775 A1* | 5/2011 | Brown | A61F 5/08 606/199 |
| 2013/0092173 A1* | 4/2013 | Alexander | A61B 1/00016 128/207.18 |
| 2014/0128761 A1* | 5/2014 | Cline | A61F 5/08 600/538 |

* cited by examiner

SPRING-BIASED NASAL MOLDING DEVICE

BACKGROUND OF THE INVENTION

This invention relates generally to the field of orthopedic appliances used to presurgically ameliorate congenital cleft lip deformities in infants by the application of direct controlled molding forces, such appliances often referred to as nasoalveolar molding (NAM) appliances, as well as to methods of correcting cleft lips using such NAM appliances.

A key component of the cleft lip deformity is nasal asymmetry and abnormal form. Current surgical techniques can achieve limited correction. Pre-surgical nasal molding has become popular in large cleft centers in an attempt to minimize the nasal deformity prior to surgery. Unlike adult cartilage, the nasal cartilages of an infant are responsive to external molding pressures and will pemanently change shape. The most common pre-surgical treatment (nasoalveolar molding) now in use is limited to linear molding changes on the nostrils, and requires an oral splint for stabilization of the nasal molding component. The traditional NAM treatment protocol requires weekly visits to the orthodontist over the first three months of life of the infant for progressive manual adjustment of the NAM device to alter the molding forces on the infant's alveolus and nasal anatomy. The traditional NAM device relies on taping across the base of the nose to achieve medial movement of the lateral crura and alar bases, and a separate pressure post based on an acrylic oral splint to fit inside the nostril and lift the nasal tip. Limitations of this existing technique are that the taping force is extremely variable in achieving the desired result, can distort the upper lip, and since the upward force is more powerful than the taping, an enlarged, iatrogenic triangulated nostril deformity can result.

Improved methodologies and nasal molding devices are disclosed in U.S. Pat. No. 9,486,353 to Hopper, U.S. Pat. No. 8,323,308 to Hopper and U.S. Pat. No. 8,523,896 to Hopper, in which a dynamic NAM device is disclosed. The device in a main embodiment comprises a pair of rotation assemblies each having an internal shaping member for insertion in a nostril and an external shaping member to be positioned externally to the nostril, wherein the internal and external shaping members are progressively incrementally pivoted about the rotation assemblies, while simultaneously the separation distance between the rotation assemblies is incrementally decreased by reducing the angular separation about a centralized assembly, thereby molding the nasal anatomy into the desired shape over time. The device requires mechanisms to lock the angular positioning of the centralized assembly and the rotational positioning of the external/internal shaping members. Furthermore, the device requires multiple manual adjustments over the course of time.

It is an object of this invention to provide a device and a method that addresses the problems encountered in the known devices and methods for presurgical molding and shaping of anatomical members distorted or improperly formed due to the presence of a cleft lip. It is a further object to provide a spring-biased nasal molding device that imparts a three-dimensional rotational change in nasal morphology in preparation for corrective surgery, which device is self-retaining and self-supporting due to opposing tension across the nose, to rotate the lateral crura and alar crease of the lower lateral cartilages of the nose medially and superiorly, while simultaneously elevating the genu and soft triangle of the nasal tip superiorly, with the simultaneous, coordinated and progressive rotational molding of the nostril width and height precluding nasal aperture distortion or enlargement. It is a further object to provide such a device that automatically and continuously provides the shaping force without need for manual adjustment after placement in the nasal anatomical members. It is a further object to provide such a device wherein the shaping force is produced by a unitary biasing member composed of a polymer material and comprising a spring segment, a pair of intra-nasal projecting members and a pair of extra-nasal arm members, with the device further comprising a cover member disposed on each of the extra-nasal arm members and a stent member disposed on each of the intra-nasal projecting members.

SUMMARY OF THE INVENTION

A spring-biased nasal molding device is presented that is an orthopedic appliance adapted for automatically and continuously shaping and molding the cartilage, tissues, etc. of the nose, upper mouth, gums and upper lip of infants having unilateral or bilateral cleft lips in order to promote symmetry and proper morphology of these anatomical features prior to the corrective surgical procedures used to close the cleft. The nasal molding device is self-supporting and self-retaining on the patient. The nasal molding device is easily sized and oriented relative to each patient.

In use the spring-biased nasal molding device is applied to the patient with the intra-nasal shaping members inserted internally into the nostrils and with the extra-nasal shaping members positioned bilaterally externally to the nostrils along the alar crease between the nasal and cheek units.

The invention is a nasal molding device adapted for pre-surgical molding of cleft lip deformities in a patient, said device comprising a biasing member, preferably a unitary biasing member, composed of a polymer material and comprising a U-shaped central spring segment, a pair of tubular intra-nasal projecting members and a pair of extra-nasal arm members, wherein said intra-nasal projecting members are connected to said central spring segment and said extra-nasal arm members are connected to said intra-nasal projecting members; a cover member disposed on each of said extra-nasal arm members, the combination of said cover members and said extra-nasal arm members defining a pair of extra-nasal shaping assemblies; a tubular stent member disposed on each of said intra-nasal projecting members, each of said stent members comprising a rounded, radially-projecting body, the combination of said stent members and said intra-nasal projecting members defining a pair of intra-nasal shaping assemblies; wherein said intra-nasal projecting members each comprise a base portion and an elongated post portion, and wherein said extra-nasal arm members are connected to said base portions of said intra-nasal projecting members; said unitary biasing member further comprising a pair of helical spring members, wherein said intra-nasal projecting members are connected to said central spring segment by said helical spring members, each of said base portions of said intra-nasal projecting members comprising a cavity, and said helical spring members being received within said cavities of said base portions of said intra-nasal projecting members; wherein said intra-nasal shaping assemblies are adapted to be positioned in the nostrils of the patient having a cleft lip deformity and said extra-nasal shaping assemblies are adapted to be positioned along the alar creases of the patient, such that the tissue of the patient is retained between the intra-nasal shaping assemblies and the extra-nasal shaping assemblies, and whereby said intra-nasal shaping assemblies are separable by manually flexing said spring segment, and whereby upon release said spring segment brings said intra-nasal shaping assemblies together over an arced pathway.

With this structure, a properly sized nasal molding device is chosen, the device possessing the desired final separation distance between the intra-nasal shaping assemblies and also possessing the desired spring strength to apply the correct amount of force to the nasal structures. The intra-nasal shaping assemblies are then spread apart by the medical practitioner and placed onto the patient such that the intra-nasal member are inserted into the nostrils and the extra-nasal members are positioned externally to the nostrils. The relationship of the intra-nasal and extra-nasal shaping assemblies in combination with biasing force of the spring member serves to retain the device on the patient without need for additional affixation and serves over time to mold and reposition the anatomical features into the desired configuration.

Alternatively, the invention may be described and defined as a nasal molding device adapted for pre-surgical molding of cleft lip deformities in a patient, said device comprising a biasing member composed of a polymer material and comprising a central spring segment, a pair of intra-nasal projecting members and a pair of extra-nasal arm members, wherein said intra-nasal projecting members are connected to said central spring segment and said extra-nasal arm members are connected to said intra-nasal projecting members; a cover member disposed on each of said extra-nasal arm members, the combination of said cover members and said extra-nasal arm members defining a pair of extra-nasal shaping assemblies; a stent member disposed on each of said intra-nasal projecting members, the combination of said stent members and said intra-nasal projecting members defining a pair of intra-nasal shaping assemblies; wherein said intra-nasal shaping assemblies are adapted to be positioned in the nostrils of the patient having a cleft lip deformity and said extra-nasal shaping assemblies are adapted to be positioned along the alar creases of the patient, such that the tissue of the patient is retained between the intra-nasal shaping assemblies and the extra-nasal shaping assemblies, and whereby said intra-nasal shaping assemblies are separable by manually flexing said spring segment, and whereby upon release said spring segment brings said intra-nasal shaping assemblies together over an arced pathway. Still further, such a device wherein said central spring member is U-shaped; wherein said intra-nasal projecting members are tubular and each comprise a base portion and an elongated post portion; wherein said intra-nasal projecting members each further comprise a retention member; wherein each of said stent members is tubular and comprises a radially-projecting body; wherein said radially-projecting bodies are rounded; wherein said radially-projecting bodies are rounded; said unitary biasing member further comprising a pair of helical spring members, wherein said intra-nasal projecting members are connected to said central spring segment by said helical spring members; and/or each of said base portions of said intra-nasal projecting members comprising a cavity, and said helical spring members being received within said cavities of said base portions of said intra-nasal projecting members.

Alternatively summarized, the invention is a nasal molding device adapted for pre-surgical molding of cleft lip deformities in a patient, said device comprising: a unitary biasing member composed of a polymer material and comprising a U-shaped central spring segment, a pair of tubular intra-nasal projecting members and a pair of extra-nasal arm members, wherein said intra-nasal projecting members are connected to said central spring segment and said extra-nasal arm members are connected to said intra-nasal projecting members; a cover member disposed on each of said extra-nasal arm members, the combination of said cover members and said extra-nasal arm members defining a pair of extra-nasal shaping assemblies; a tubular stent member disposed on each of said intra-nasal projecting members, the combination of said stent members and said intra-nasal projecting members defining a pair of intra-nasal shaping assemblies; wherein said intra-nasal shaping assemblies are adapted to be positioned in the nostrils of the patient having a cleft lip deformity and said extra-nasal shaping assemblies are adapted to be positioned along the alar creases of the patient, such that the tissue of the patient is retained between the intra-nasal shaping assemblies and the extra-nasal shaping assemblies, and whereby said intra-nasal shaping assemblies are separable by manually flexing said spring segment, and whereby upon release said spring segment brings said intra-nasal shaping assemblies together over an arced pathway. Still further, such a device wherein said intra-nasal projecting members each comprise a base portion and an elongated post portion, and wherein said extra-nasal arm members are connected to said base portions of said intra-nasal projecting members; wherein each of said stent members comprises a rounded, radially-projecting body; said unitary biasing member further comprising a pair of helical spring members, wherein said intra-nasal projecting members are connected to said central spring segment by said helical spring members; each of said base portions of said intra-nasal projecting members comprising a cavity, and said helical spring members being received within said cavities of said base portions of said intra-nasal projecting members.

Still further alternatively summarized, the invention is a nasal molding device adapted for pre-surgical molding of cleft lip deformities in a patient, said device comprising a biasing member composed of a polymer material and comprising a U-shaped central spring segment, a pair of tubular intra-nasal projecting members and a pair of extra-nasal arm members, wherein said intra-nasal projecting members are connected to said central spring segment and said extra-nasal arm members are connected to said intra-nasal projecting members; a cover member disposed on each of said extra-nasal arm members, the combination of said cover members and said extra-nasal arm members defining a pair of extra-nasal shaping assemblies; a tubular stent member disposed on each of said intra-nasal projecting members, each of said stent members comprising a rounded, radially-projecting body, the combination of said stent members and said intra-nasal projecting members defining a pair of intra-nasal shaping assemblies; wherein said intra-nasal projecting members each comprise a base portion and an elongated post portion, and wherein said extra-nasal min members are connected to said base portions of said intra-nasal projecting members; said biasing member further comprising a pair of helical spring members, wherein said intra-nasal projecting members are connected to said central spring segment by said helical spring members, each of said base portions of said intra-nasal projecting members comprising a cavity, and said helical spring members being received within said cavities of said base portions of said intra-nasal projecting members; wherein said intra-nasal shaping assemblies are adapted to be positioned in the nostrils of the patient having a cleft lip deformity and said extra-nasal shaping assemblies are adapted to be positioned along the alar creases of the patient, such that the tissue of the patient is retained between the intra-nasal shaping assemblies and the extra-nasal shaping assemblies, and whereby said intra-nasal shaping assemblies are separable by manually flexing said spring segment, and whereby upon release said spring segment brings said intra-nasal shaping assemblies together over an arced pathway and/or further wherein said biasing member is a unitary biasing member.

DETAILED DESCRIPTION OF THE INVENTION

With reference to the drawings, the spring-biased nasal molding device or appliance will now be described in detail with regard for the best mode and preferred embodiment or embodiments, along with its method of use in correcting cleft lips. In general, the nasal molding device is an orthopedic appliance structured and adapted for shaping and molding the cartilage, tissues, etc. of the nose, upper mouth, gums and upper lip of infants having unilateral or bilateral cleft lips in order to promote symmetry and proper morphology of these anatomical features prior to the corrective surgical procedures used to close the cleft. The nasal molding device is self-supporting and self-retaining on the patient, such that the need for adhesive tape or elastic members to maintain the device on the patient is obviated or greatly minimized. The nasal molding device is easily sized and oriented relative to each patient, and the device applies continuous pressure during the corrective process.

Embodiments of the invention are shown in FIGS. 1 through 6, wherein the device comprises a biasing member 10, and most preferably a unitary biasing member 10. The term "unitary" shall be taken to mean a member formed as a single piece, preferably formed of a polymer material and shaped by molding, CAD sculpting, 3-D laser deposition printing, rapid prototyping of the like. The biasing member 10 is flexible such that it may be flexed or tensioned in order to create a biasing force that is then transferred to the patient.

Figure 1:
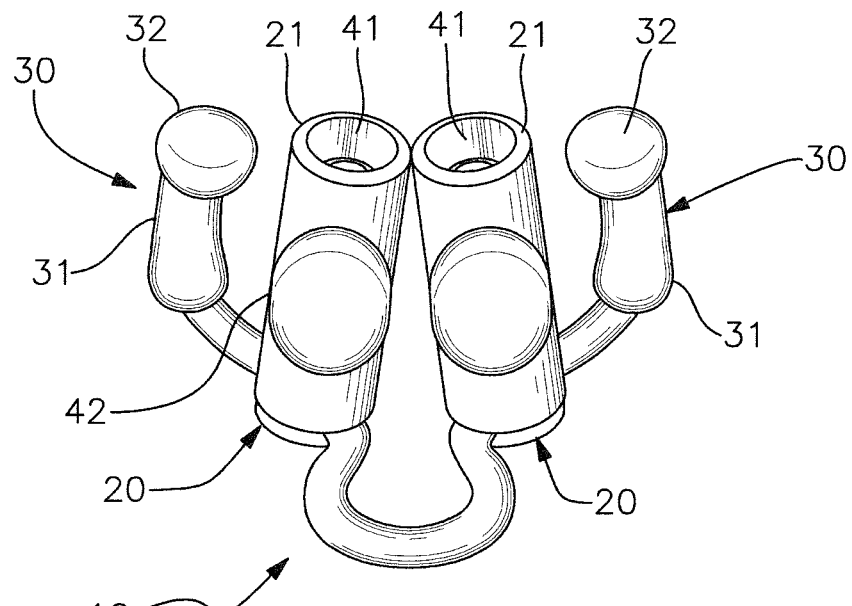
FIG. 1 is a perspective view of an embodiment of the invention comprising a unitary biasing member.
Figure 2:
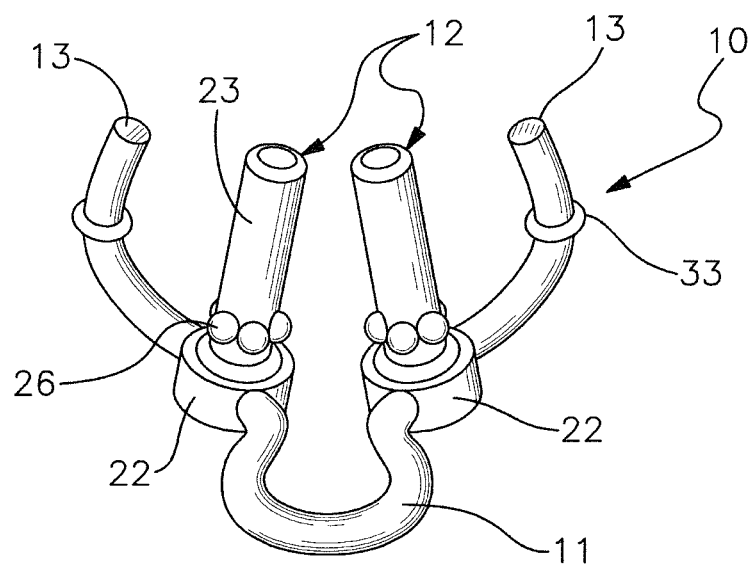
FIG. 2 illustrates the unitary biasing member of the embodiment of FIG. 1.

In a basic embodiment as shown in FIGS. 1 and 2, the biasing member 10 comprises a U-shaped central spring segment 11, a pair of intra-nasal projecting members 12, preferably tubular, and a pair of extra-nasal arm members 13, wherein the intra-nasal projecting members 12 are connected to the central spring segment 11 and the extra-nasal win members 13 are connected to the intra-nasal projecting members 12, preferably formed as a single member and defining a unitary biasing member 10.

The extra-nasal arm members 13 are preferably elongated post members and may be provided with retention members 33 to retain a cover member 31, preferably removably disposed coaxially on each of the extra-nasal arm members 13, the combination of the cover members 31 and the extra-nasal arm members 13 defining a pair of extra-nasal shaping assemblies 30. The cover members 31 are preferably formed of a compressible, biocompatible polymer material, and may be provided with an enlarged tip 32.

Figure 5:
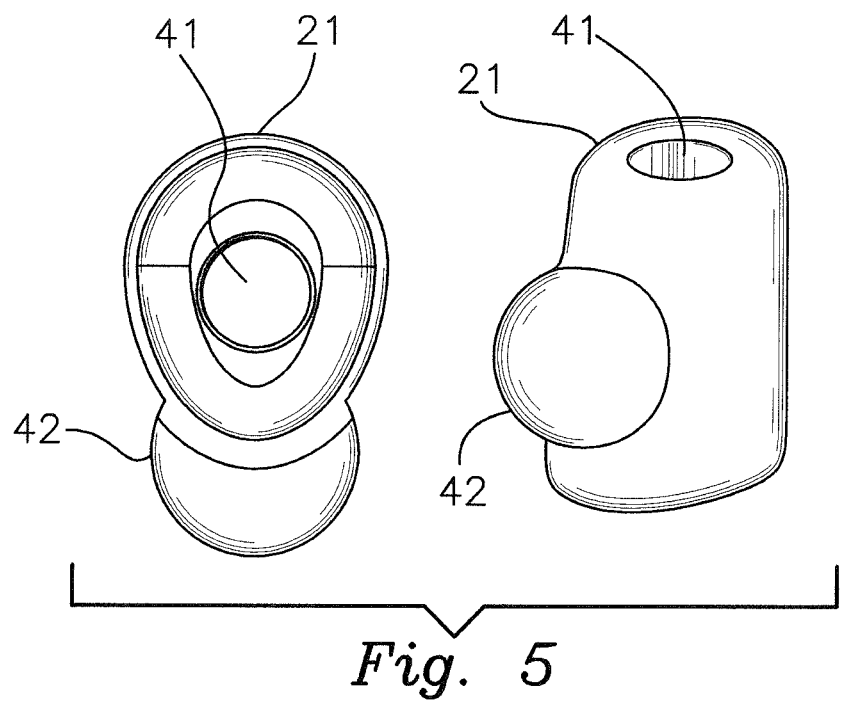
FIG. 5 is an illustration of an embodiment of the tubular stent member.
Figure 6:
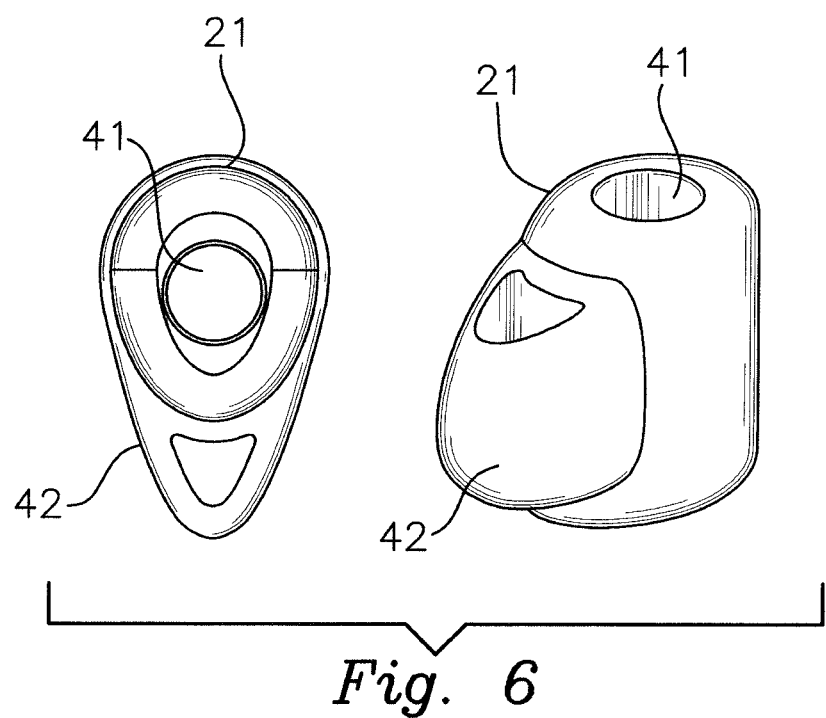
FIG. 6 is an illustration of an alternative embodiment of the tubular stent member.

A stent member 21, preferably tubular, is disposed on each of the intra-nasal projecting members 12, each of the stent members 21 preferably comprising a hollow core 41 and a bulbous or rounded, radially-projecting body 42, as shown in FIGS. 5 and 6, the combination of the stent members 21 and the intra-nasal projecting members 12 defining a pair of intra-nasal shaping assemblies 20. Tubular intra-nasal projecting members 12 and tubular stent members 21 are preferred to allow for passage of air through the members. The radially-projecting bodies 42 extend the nostrils in the desired directions when the device is in use. Preferably the stent members 21 are removable and replaceable, and may be rotated on the projecting members 12 as desired. Different sized stent members 21 may be utilized. The stent members 21 are preferably formed of a compressible, biocompatible polymer material.

The intra-nasal projecting members 12 may each comprise a widened base portion 22 and an elongated post portion 23, such that the extra-nasal arm members 13 are connected to the base portions 22 of the intra-nasal projecting members 12. The post portions 23 of the intra-nasal projecting members 12 may be provided with retention members 26 to better secure the stent members 21.

Figure 3:
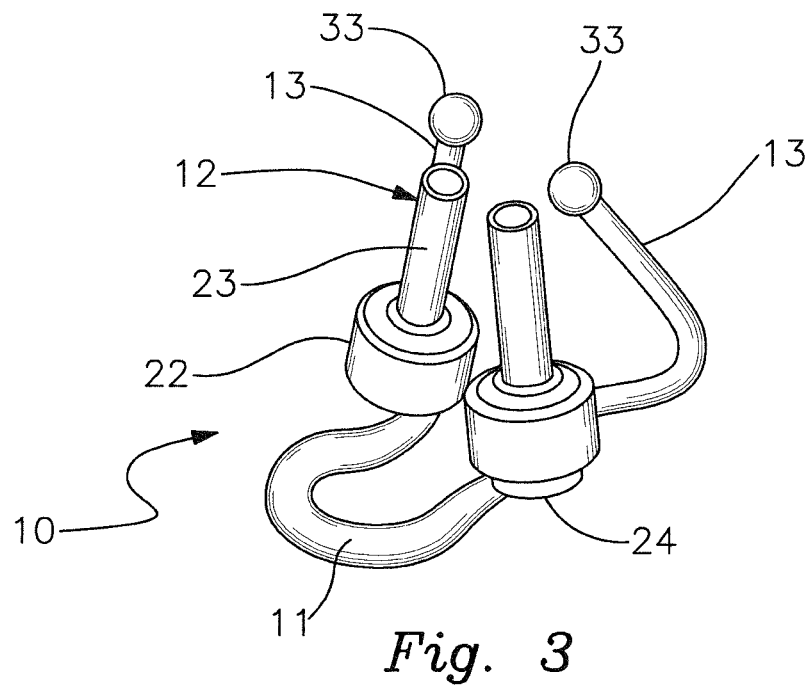
FIG. 3 is a perspective view of another embodiment of the invention comprising a unitary biasing member having a pair of helical spring members in addition to a U-shaped central spring segment.
Figure 4:
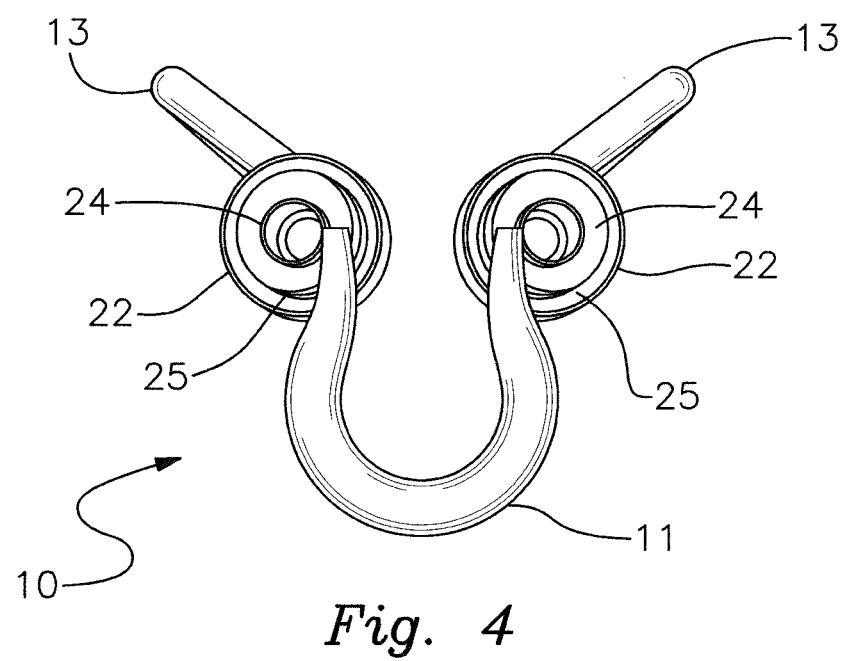
FIG. 4 is a bottom view of the embodiment of FIG. 3.

In another alternative embodiment shown in FIGS. 3 and 4, the biasing member 10 further comprises a pair of helical coil spring members 24, the helical coil springs 24 connecting the intra-nasal projecting members 12 to the central spring segment 12. Preferably, the biasing member 10 of this embodiment is formed as a unitary biasing member 10. In a preferred embodiment, the based portions 22 each comprise a recess or cavity 25, such that the helical coil spring members 24 extend into and are received within the cavity 25 of the base portions 22. The combination of the central spring segment 11 and the helical coil spring members 24 enables the unitary biasing member 10 to have a plurality of tensions, such that the extra-nasal shaping assemblies 30 can be rotated and tensioned relative to the intra-nasal shaping assemblies 20 independently of the tension provided by the central spring segment 11, or such that the combination of the three springs 11 and 24 provides tensioning about multiple tension focal points.

It is contemplated that certain equivalents or substations for elements set forth above may be obvious to those of ordinary skill in the art, and therefore the true scope and definition of the invention is to be as set forth in the following claims.

We claim:

1. A nasal molding device adapted for pre-surgical molding of cleft lip deformities in a patient, said device comprising:

a biasing member composed of a polymer material and comprising a central spring segment, a pair of tubular intra-nasal projecting members having two open ends and a pair of extra-nasal arm members, wherein said intra-nasal projecting members are connected to said central spring segment and said extra-nasal arm members are connected to said intra-nasal projecting members;

a cover member disposed on each of said extra-nasal arm members, the combination of said cover members and said extra-nasal arm members defining a pair of extra-nasal shaping assemblies;

a tubular stent member disposed on each of said intra-nasal projecting members, each said stent member having a hollow core with two open ends, the combination of said stent members and said intra-nasal projecting members defining a pair of intra-nasal shaping assemblies;

wherein said intra-nasal shaping assemblies are adapted to be positioned in the nostrils of the patient having a cleft lip deformity and said extra-nasal shaping assemblies are adapted to be positioned along the alar creases of the patient, such that the tissue of the patient is retained between the intra-nasal shaping assemblies and the extra-nasal shaping assemblies, and whereby said intra-nasal shaping assemblies are separable by manually flexing said spring segment, and whereby upon release said spring segment brings said intra-nasal shaping assemblies together over an arced pathway.

2. The device of claim 1, wherein said central spring segment is U-shaped.

3. The device of claim 2, wherein said intra-nasal projecting members each comprise a base portion and an elongated post portion.

4. The device of claim 3, wherein said intra-nasal projecting members each further comprise a retention member.

5. The device of claim 2, wherein each of said stent members comprises a bulbous, radially-projecting body.

6. The device of claim 5, wherein said radially-projecting bodies are rounded.

7. The device of claim 2, said biasing member further comprising a pair of helical spring members, wherein said intra-nasal projecting members are connected to said central spring segment by said helical spring members.

8. The device of claim 1, wherein said intra-nasal projecting members each comprise a base portion and an elongated post portion.

9. The device of claim 8, wherein said intra-nasal projecting members each further comprise a retention member.

10. The device of claim 8, said biasing member further comprising a pair of helical spring members, wherein said intra-nasal projecting members are connected to said central spring segment by said helical spring members, each of said base portions of said intra-nasal projecting members comprising a cavity, and said helical spring members being received within said cavities of said base portions of said intra-nasal projecting members.

11. The device of claim 1, wherein each of said stent members comprises a bulbous, radially-projecting body.

12. The device of claim 11, wherein said radially-projecting bodies are rounded.

13. The device of claim 1, said biasing member further comprising a pair of helical spring members, wherein said intra-nasal projecting members are connected to said central spring segment by said helical spring members.

14. A nasal molding device adapted for pre-surgical molding of cleft lip deformities in a patient, said device comprising:

a unitary biasing member composed of a polymer material and comprising a U-shaped central spring segment, a pair of tubular intra-nasal projecting members having two open ends and a pair of extra-nasal arm members, wherein said intra-nasal projecting members are connected to said central spring segment and said extra-nasal arm members are connected to said intra-nasal projecting members;

a cover member disposed on each of said extra-nasal arm members, the combination of said cover members and said extra-nasal arm members defining a pair of extra-nasal shaping assemblies;

a tubular stent member disposed on each of said intra-nasal projecting members, each said stent member having a hollow core with two open ends, the combination of said stent members and said intra-nasal projecting members defining a pair of intra-nasal shaping assemblies;

wherein said intra-nasal shaping assemblies are adapted to be positioned in the nostrils of the patient having a cleft lip deformity and said extra-nasal shaping assemblies are adapted to be positioned along the alar creases of the patient, such that the tissue of the patient is retained between the intra-nasal shaping assemblies and the extra-nasal shaping assemblies, and whereby said intra-nasal shaping assemblies are separable by manually flexing said spring segment, and whereby upon release said spring segment brings said intra-nasal shaping assemblies together over an arced pathway.

15. The device of claim 14, wherein said intra-nasal projecting members each comprise a base portion and an elongated post portion, and wherein said extra-nasal arm members are connected to said base portions of said intra-nasal projecting members.

16. The device of claim 15, said unitary biasing member further comprising a pair of helical spring members, wherein said intra-nasal projecting members are connected to said central spring segment by said helical spring members, each of said base portions of said intra-nasal projecting members comprising a cavity, and said helical spring members being received within said cavities of said base portions of said intra-nasal projecting members.

17. The device of claim 16, wherein each of said stent members comprises a rounded, bulbous, radially-projecting body.

18. The device of claim 14, wherein each of said stent members comprises a rounded, bulbous, radially-projecting body.

19. The device of claim 14, said unitary biasing member further comprising a pair of helical spring members, wherein said intra-nasal projecting members are connected to said central spring segment by said helical spring members.

20. A nasal molding device adapted for pre-surgical molding of cleft lip deformities in a patient, said device comprising:

a biasing member composed of a polymer material and comprising a U-shaped central spring segment, a pair of tubular intra-nasal projecting members having two open ends and a pair of extra-nasal arm members, wherein said intra-nasal projecting members are connected to said central spring segment and said extra-nasal arm members are connected to said intra-nasal projecting members;

a cover member disposed on each of said extra-nasal arm members, the combination of said cover members and said extra-nasal arm members defining a pair of extra-nasal shaping assemblies;

a tubular stent member disposed on each of said intra-nasal projecting members, each of said stent members comprising a hollow core with two open ends and a rounded, bulbous, radially-projecting body, the combination of said stent members and said intra-nasal projecting members defining a pair of intra-nasal shaping assemblies;

wherein said intra-nasal projecting members each comprise a base portion and an elongated post portion, and wherein said extra-nasal arm members are connected to said base portions of said intra-nasal projecting members;

said biasing member further comprising a pair of helical spring members, wherein said intra-nasal projecting members are connected to said central spring segment by said helical spring members, each of said base portions of said intra-nasal projecting members comprising a cavity, and said helical spring members being received within said cavities of said base portions of said intra-nasal projecting members;

wherein said intra-nasal shaping assemblies are adapted to be positioned in the nostrils of the patient having a cleft lip deformity and said extra-nasal shaping assemblies are adapted to be positioned along the alar creases of the patient, such that the tissue of the patient is retained between the intra-nasal shaping assemblies and the extra-nasal shaping assemblies, and whereby said intra-nasal shaping assemblies are separable by manually flexing said spring segment, and whereby upon release said spring segment brings said intra-nasal shaping assemblies together over an arced pathway.

* * * * *